United States Patent
Lee-Huang et al.

(10) Patent No.: US 8,911,935 B2
(45) Date of Patent: Dec. 16, 2014

(54) MITOCHONDRIA AND HUMAN IMMUNODEFIENCY VIRUS TYPE 1

(71) Applicants: Sylvia Lee-Huang, New York, NY (US); Paul Huang, Boston, MA (US); Philip Huang, Maple Glen, PA (US)

(72) Inventors: Sylvia Lee-Huang, New York, NY (US); Paul Huang, Boston, MA (US); Philip Huang, Maple Glen, PA (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 13/654,003

(22) Filed: Oct. 17, 2012

(65) Prior Publication Data

US 2013/0096086 A1   Apr. 18, 2013

Related U.S. Application Data

(60) Provisional application No. 61/547,925, filed on Oct. 17, 2011.

(51) Int. Cl.
| | |
|---|---|
| *C12Q 1/02* | (2006.01) |
| *C12Q 1/18* | (2006.01) |
| *C12Q 1/70* | (2006.01) |
| *A61K 31/353* | (2006.01) |
| *A61K 31/365* | (2006.01) |
| *A61K 45/06* | (2006.01) |
| *A61K 31/277* | (2006.01) |
| *A61K 31/69* | (2006.01) |

(52) U.S. Cl.
CPC .............. *C12Q 1/025* (2013.01); *A61K 31/353* (2013.01); *A61K 31/365* (2013.01); *A61K 45/06* (2013.01); *A61K 31/277* (2013.01); *A61K 31/69* (2013.01)
USPC ................................. 435/5; 435/29; 435/325

(58) Field of Classification Search
CPC ... C12Q 1/025; A61K 31/277; A61K 31/353; A61K 31/365; A61K 31/69
See application file for complete search history.

(56) References Cited

FOREIGN PATENT DOCUMENTS

WO   2006032085   3/2006

OTHER PUBLICATIONS

Muratori et al. Human immunodeficiency virus type 1 (HIV-1) protease inhibitors block cell-to-cell HIV-1 endocytosis in dendritic cells. Journal of General Virology 2009, vol. 90, pp. 2777-2787.*
Jiang et al. HIV antiretroviral drug combination induces endothelial mitochondrial dysfunction and reactive oxygen species production, but not apoptosis. Toxicology and Applied Pharmacology 2007, vol. 224, pp. 60-71.*
Ratajczak et al. Membrane-derived microvesicles: important and underappreciated mediators of cell-to-cell communication. Leukemia 2006, vol. 20, pp. 1487-1495.*
Srivastava et al. Optimization of unique, unchanged thioesters as inhibitors of HIV replication. Bioorganic & Medicinal Chemistry 2004, vol. 12, pp. 6437-6450.*
Alvero et al., "Targeting the mitochondria activates two independent cell death pathways in ovarian cancer stem cells", Mol Cancer Ther, 2011, vol. 10, pp. 1385-1393.
Chen et al., "Predominant mode of human immunodeficiency virus transfer between T cells is mediated by sustained Env-dependent neutralization-resistant virological synapses", J Virol, 2007, vol. 81, pp. 12582-12595.
Cote et al., "Changes in mitochondrial DNA as a marker of nucleoside toxicity in HIV-infected patients", N Engl J Med, 2002, vol. 346, pp. 811-820.
Watkins et al., "Syncytium formation induced by human immunodeficiency virus type 1 isolates correlates with affinity for CD4", J Gen Virol, 1997, vol. 78, pp. 2513-2522.
Eugenin et al., "Tunneling nanotubes (TNT) are induced by HIV-infection of macrophages: A potential mechanism for intercellular HIV trafficking", Cell Immunol, 2009, vol. 254, pp. 142-148.
Galluzzi et al., "Mitochondria as therapeutic targets for cancer chemotherapy", Oncogene, 2006, vol. 25, pp. 4812-4830.
Hubner et al., "Quantitative 3D video microscopy of HIV transfer across T cell virological synapses", Science, 2009, vol. 323, pp. 1743-1747.
Lee-Huang et al., "Discovery of small-molecule HIV-1 fusion and integrase inhibitors oleuropein and hydroxytyrosol: I. fusion inhibition", Biochemical and Biophysical Res Commun, 2007, vol. 354, pp. 872-878.
Ling et al., "Reactive oxygen species generation and mitochondrial dysfunction in the apoptotic response to bortezomib, a novel proteasome inhibitor, in human H460 non-small cell lung cancer cells, The Journal of Biological Chemistry", The Journal of Biological Chemistry, 2003, vol. 278, pp. 33714-33723.
Miro et al., "Mitochondrial effects of HIV infection on the peripheral blood mononuclear cells of HIV-infected patients who were never treated with antiretrovirals", Clinical Infectious Diseases, 2004, vol. 39, pp. 710-716.
Rehman et al., "Inhibition of mitochondrial fission prevents cell cycle progression in lung cancer", The FASEB Journal, 2012, vol. 26, pp. 1-12.
Rudnicka et al., "Simultaneous cell-to-cell transmission of human immunodeficiency virus to multiple targets through polysynapses". J Virol, 2009, vol. 83, pp. 6234-6246.

(Continued)

*Primary Examiner* — Louise Humphrey
(74) *Attorney, Agent, or Firm* — Klauber & Jackson LLC

(57) ABSTRACT

Methods described herein relate to mitochondria and their role in Human immunodeficiency virus type 1 (HIV-1) infection and cell-to-cell HIV-1 transmission and compositions and methods for modulating mitochondrial mediated cell-to-cell transmission of HIV-1. Methods for screening to identify inhibitors of mitochondrial mediated cell-to-cell transmission of HIV-1 are also envisioned herein.

10 Claims, 4 Drawing Sheets

(4 of 4 Drawing Sheet(s) Filed in Color)

(56) References Cited

OTHER PUBLICATIONS

Sherer et al., "Retroviruses can establish filopodial bridges for efficient cell-to-cell transmission", Nat Cell Biol, 2007, vol. 9, pp. 310-315.

Sato et al., "Cell-to-cell spread of HIV-1 occurs within minutes and may not involve the participation of virus particles", Virology, 1992, vol. 186, pp. 712-724.

Lee-Huang et al., "Structural and functional modeling of human lysozyme reveals a unique nonapeptide, HL9, with anti-HIV activity", Biochemistry, 2005, vol. 44, pp. 4648-4655.

Guillery et al., "Modulation of mitochondrial morphology by bioenergetics defects in primary human fibroblasts", Neuromuscul Disord, 2008, vol. 18, pp. 319-330.

Meeusen et al., Mitochondrial fusion intermediates revealed in vitro, Science, 2004, vol. 305, pp. 1747-1752.

* cited by examiner

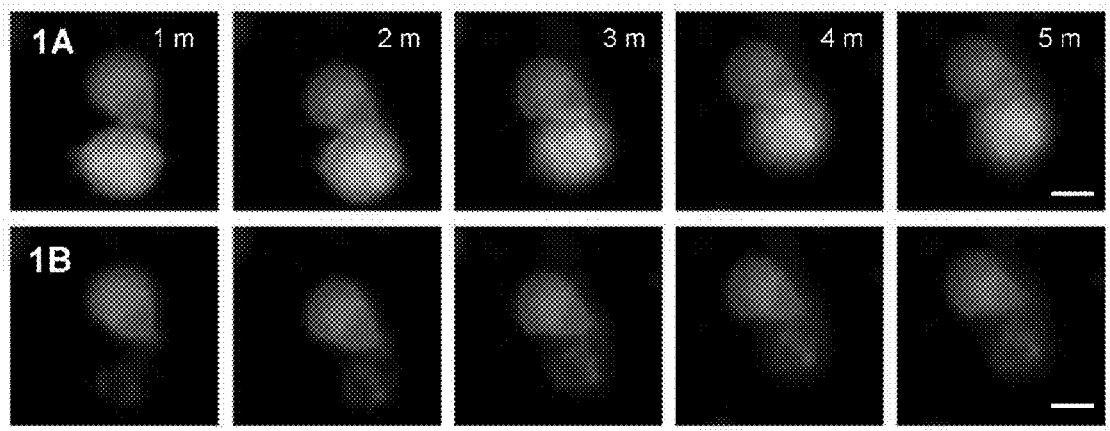
Figures 1A-B

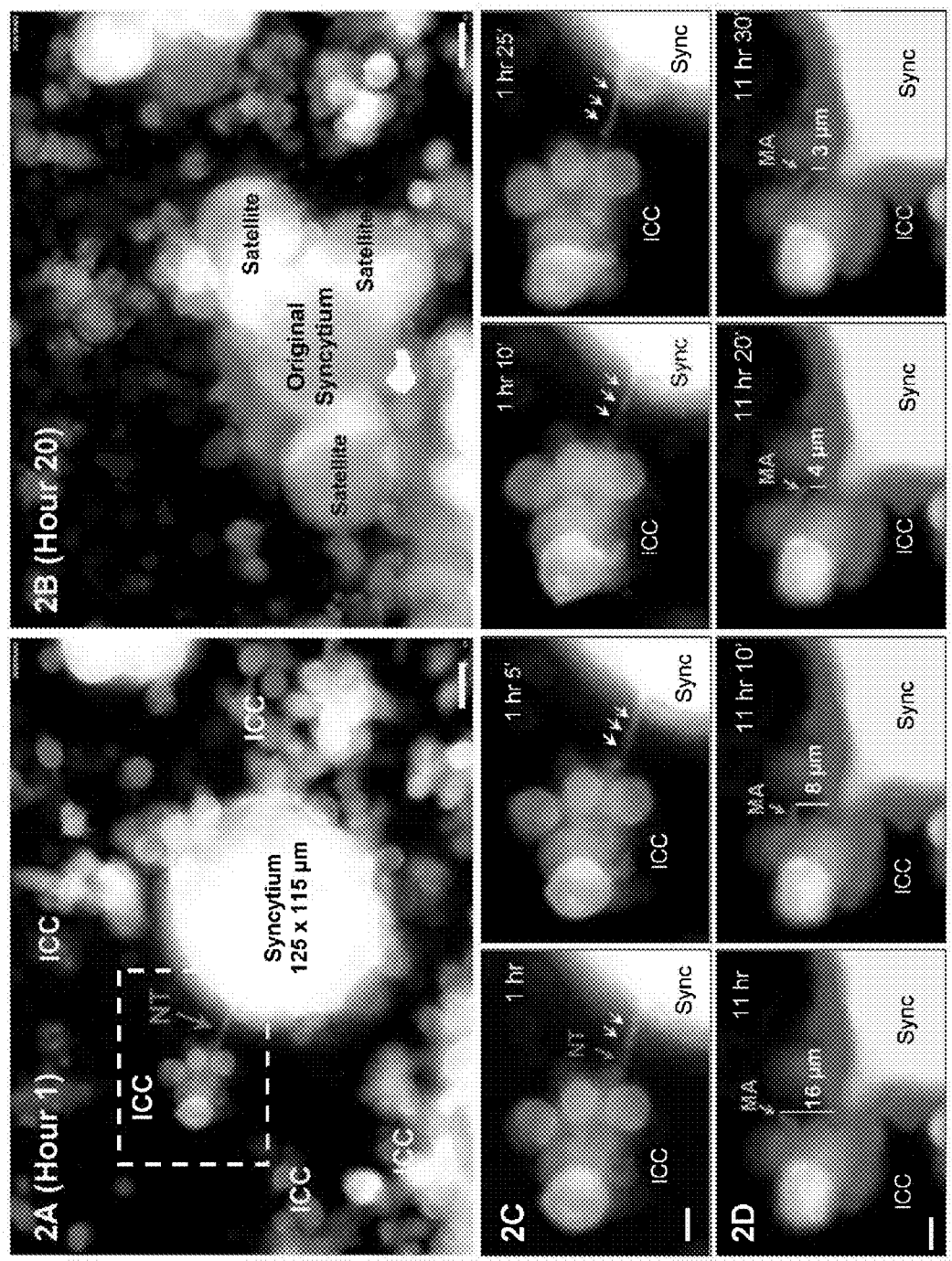
Figures 2A-D

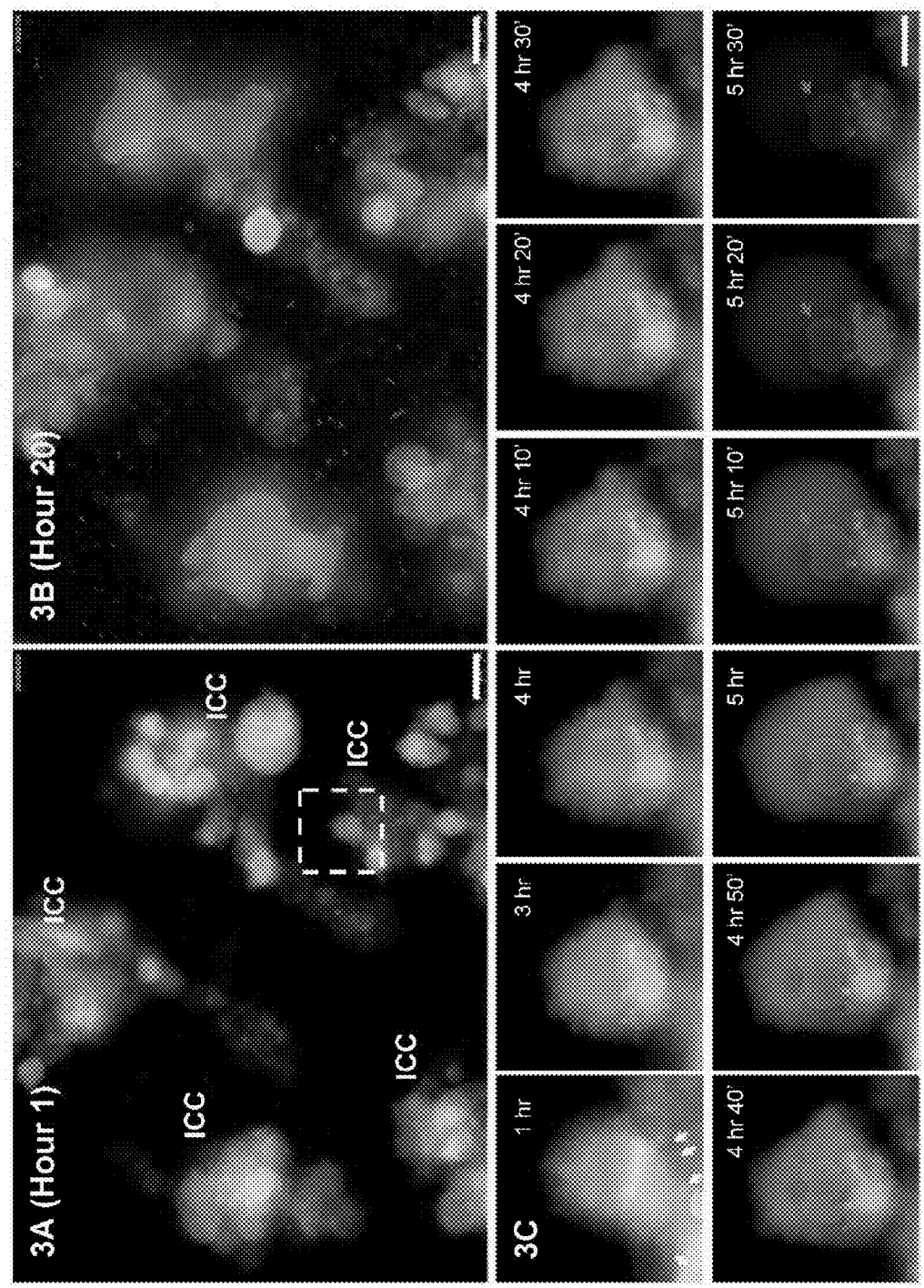
Figures 3A-C

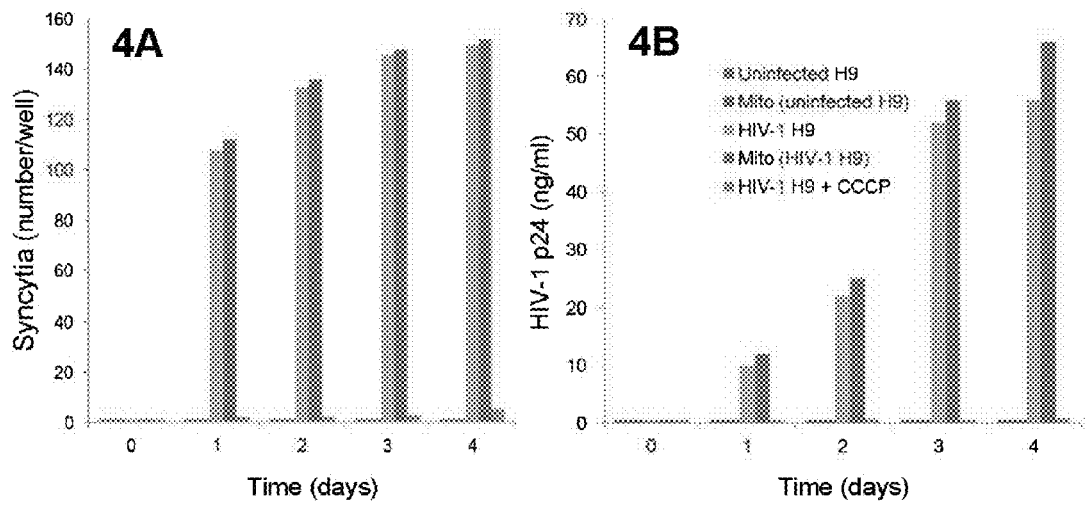
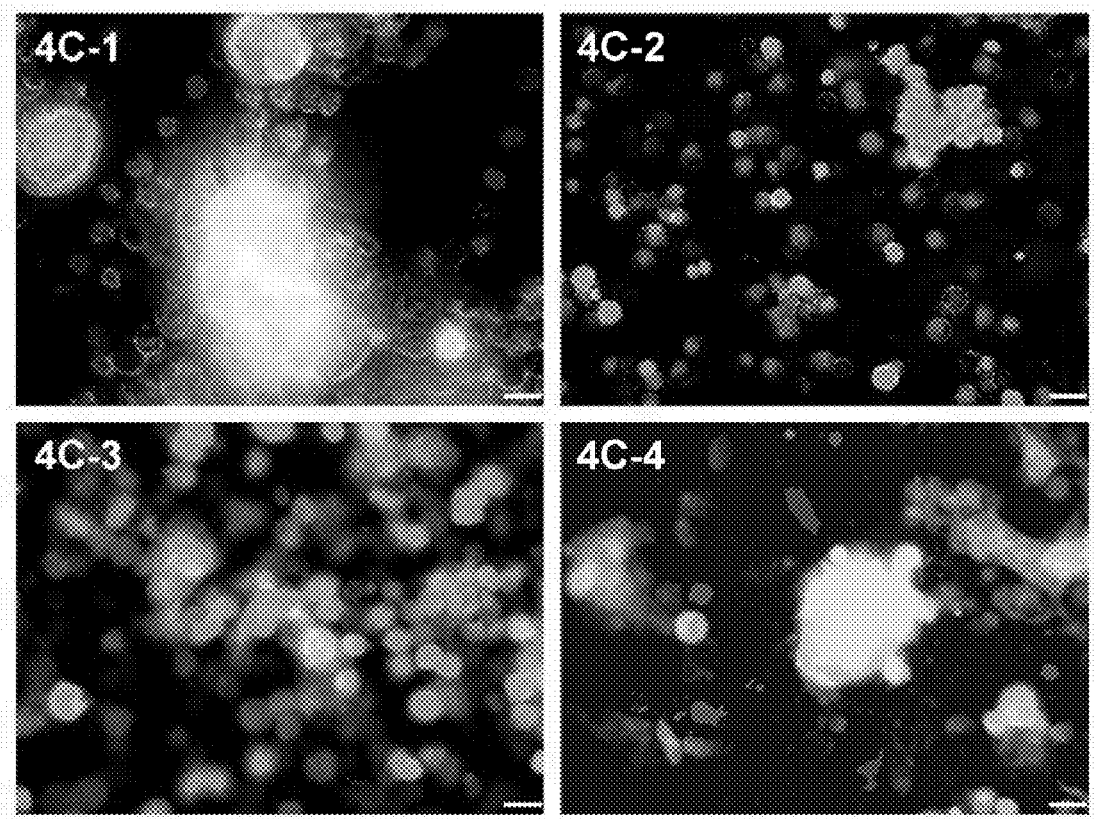
Figures 4A-C

MITOCHONDRIA AND HUMAN IMMUNODEFIENCY VIRUS TYPE 1

CROSS REFERENCE TO RELATED APPLICATIONS

This application claims priority under 35 USC §119(e) from U.S. Provisional Application Ser. No. 61/547,925, filed Oct. 17, 2011, which application is herein specifically incorporated by reference in its entirety.

FIELD OF INVENTION

The present invention generally relates to the technical fields of virology and cellular biology. More particularly, the methods described herein relate to mitochondria and their role in Human immunodeficiency virus type 1 (HIV-1) infection and transmission and compositions and methods for modulating mitochondrial mediated infection and transmission of HIV-1.

BACKGROUND OF INVENTION

AIDS (acquired immunodeficiency syndrome) is one of the leading causes of death in the developing world. HIV-1, a retrovirus which is a member of the lentivirus subfamily, is the etiologic agent of AIDS. The Lentiviridae include non-oncogenic retroviruses which usually infect cells of the immune system, particularly macrophages and T cells, causing persistent infections in diseases with long incubation periods and cytopathic effects in infected cells, such as syncytia and cell death. Lentiviral infections are not cleared by the immune system, and lead to accumulated immunologic damage over a period of many years.

HIV-1 comprises an RNA genome and exhibits reverse transcriptase activity. During its growth cycle, HIV-1 copies its RNA into proviral DNA, which is able to integrate into the chromosomal DNA of the host cell (provirus). Due to its retroviral nature and the small size of its genome, HIV-1 replication is strongly dependent on the host's cell machinery. Thus, HIV uses the transcriptional and translational machinery of the host to express viral RNA and proteins and ultimately to release mature viruses from the cell by budding from the cytoplasmic membrane. Viral replication of HIV-1 results in the death of host's helper T cells, which leads to a state of severe immunodeficiency (AIDS), to the development of various malignancies and opportunistic infections, and ultimately to the death of the infected organism.

HIV-1 is capable of infecting human host cells both through free viral particles and through cell-to-cell transmission [1, 2]. Cell-to-cell spread is up to 10,000 times more efficient than free viral infection, because virus is shielded from cellular and immunological barriers [3, 4, 5]. Several distinct modes of cell-to-cell HIV-1 dissemination have been reported, including virological synapses (VS) [6, 7], syncytia [8], filopodial bridges [9], and nanotubes [10].

Accordingly, the results presented herein elucidate certain of the mechanisms involved in cell-to-cell transmission of HIV-1.

The citation of references herein shall not be construed as an admission that such is prior art to the present invention.

Several publications and patent documents are referenced in this application in order to more fully describe the state of the art to which this invention pertains. The disclosure of each of these publications and documents is incorporated by reference herein.

SUMMARY OF THE INVENTION

The present inventors used live-cell, real-time fluorescence imaging of co-cultures of HIV-1 infected T cells and uninfected target cells to examine the action of mitochondria during cell-to-cell transmission of the virus. As described herein, mitochondria of HIV-1 infected cells enter uninfected target cells and advance viral spread. The present inventors, moreover, show that human mitochondria serve as viral reservoirs and carriers that can move between cells. Results presented herein also show that purified mitochondria from HIV-1 infected cells are infectious, and that mitochondrial inhibitors block HIV-1 transmission. Viral infection and replication in the target cells were verified by syncytial formation and HIV-1 core protein p24 production. An appreciation of the contribution of mitochondria to these processes offers new insights into the cellular mechanisms of viral transmission and identifies mitochondria as novel host targets for viral infection.

In accordance with the present discoveries, a method for screening to identify a compound for treating a subject infected with human immunodeficiency virus type 1 (HIV-1) is presented, the method comprising contacting HIV-1 infected cells and target cells with a candidate compound, wherein the target cells are susceptible to HIV-1 infection; and measuring cell-to-cell transmission of HIV-1 in the presence and absence of the candidate compound, wherein a reduction in cell-to-cell transmission of HIV-1 in the presence of the candidate compound relative to the absence of the candidate compound indicates that the candidate compound or agent is a therapeutic agent for treating the subject infected with HIV-1.

In a particular embodiment, the candidate compound is a mitochondrial inhibitor or a compound suspected to exhibit properties of a mitochondrial inhibitor. In a further embodiment thereof, the mitochondrial inhibitor is ME-344. In a more particular embodiment, the candidate compound is a mitochondrial inhibitor and a protease inhibitor. An exemplary compound exhibiting mitochondrial and protease inhibitor activity is bortezomib.

In another embodiment, the candidate compound is a modulator of cytoskeletal processes or is a compound suspected to exhibit such properties. Such cytoskeletal processes include those relating to or associated with actin or microtubule polymerization or depolymerization.

As described herein, cell-to-cell transmission of HIV-1 may be measured by tracking mitochondrial movement from HIV-1 infected cells to the target cells. Measuring cell-to-cell transmission of HIV-1 may further comprise an assessment of virological synapse and syncytia formation.

In a further aspect, a method for screening to identify a compound that inhibits human immunodeficiency virus type 1 (HIV-1) uptake by mitochondria is presented, the method comprising contacting HIV-1 infected cells and target cells with a candidate compound, wherein the target cells are susceptible to HIV-1 infection; and measuring uptake of HIV-1 by mitochondria in the target cells in the presence and absence of the candidate compound, wherein a reduction in uptake of HIV-1 by mitochondria in the target cells in the presence of the candidate compound relative to the absence of the candidate compound indicates that the candidate compound is an inhibitor of HIV-1 uptake by the mitochondria.

In an embodiment of the method, the candidate compound inhibits viral fusion or is a compound suspected to exhibit such properties. Exemplary such compounds include enfuvirtide (Fuzeon) and maraviroc (Selzentry). In another embodiment, the candidate compound inhibits activity of viral fusion protein gp41 or is a compound suspected to exhibit such properties. In yet another embodiment, the candidate compound inhibits activity of mitochondrial fusion proteins or is a compound suspected to exhibit such properties.

As described herein, measuring uptake of HIV-1 by mitochondria in the target cells may be determined by isolating mitochondria from the target cells following contact with HIV-1 infected cells in the presence or absence of the candidate compound and determining and comparing infectivity of mitochondria isolated from target cells contacted with the candidate compound to infectivity of mitochondria isolated from target cells not contacted with the candidate compound, wherein decreased infectivity in the mitochondria isolated from target cells contacted with the candidate compound indicates that the candidate compound is an inhibitor of HIV-1 uptake by the mitochondria.

Also encompassed herein is a method for identifying a compound with anti-HIV-1 activity, the method comprising contacting HIV-1 infected cells and target cells with a candidate compound, wherein the target cells are susceptible to HIV-1 infection; and measuring cell-to-cell transmission of HIV-1 in the presence and absence of the candidate compound, wherein a reduction in cell-to-cell transmission of HIV-1 in the presence of the candidate compound relative to the absence of the candidate compound identifies the candidate compound as a compound with anti-HIV-1 activity. In a particular embodiment, the candidate compound belongs to a class of mitochondrial inhibitors.

Also encompassed herein is a method for treating a subject infected with human immunodeficiency virus type 1 (HIV-1), the method comprising administering to the subject a mitochondrial inhibitor in a therapeutically effective amount, wherein the therapeutically effective amount is sufficient to reduce or inhibit cell-to-cell mediated transmission of HIV-1, thereby treating the subject infected HIV-1. In a particular embodiment thereof, the mitochondrial inhibitor is ME-344, carbonyl cyanide m-chlorophenyl hydrazone (CCCP), antimycin A, or oligomycin. In another embodiment, the mitochondrial inhibitor does not exhibit the ability to inhibit nucleoside or nucleotide transcriptase activity. In yet another embodiment, the mitochondrial inhibitor is also a proteosome inhibitor. An exemplary such mitochondrial and proteosome inhibitor is bortezomib.

In a further aspect, the method may further comprise treating the subject with a therapeutic agent used for treating subjects infected with HIV-1, including, without limitation, nucleoside analogue reverse transcriptase inhibitors and either of a protease inhibitor or a non-nucleoside reverse transcriptase inhibitor.

In a further aspect, a method for reducing cell-to-cell mediated transmission of HIV-1 in a subject infected with human immunodeficiency virus type 1 (HIV-1) is presented, the method comprising administering to the subject a mitochondrial inhibitor in a therapeutically effective amount, wherein the therapeutically effective amount is sufficient to reduce or inhibit cell-to-cell mediated transmission of HIV-1, thereby reducing cell-to-cell mediated transmission of HIV-1 in the subject infected HIV-1. In a particular embodiment thereof, the mitochondrial inhibitor is ME-344, carbonyl cyanide m-chlorophenyl hydrazone (CCCP), antimycin A, or oligomycin. In another embodiment, the mitochondrial inhibitor does not exhibit the ability to inhibit nucleoside or nucleotide transcriptase activity. In yet another embodiment, the mitochondrial inhibitor is also a proteosome inhibitor. An exemplary such mitochondrial and proteosome inhibitor is bortezomib. The method may further comprise treating the subject with a therapeutic agent used for treating subjects infected with HIV-1, including, without limitation, nucleoside analogue reverse transcriptase inhibitors and either of a protease inhibitor or a non-nucleoside reverse transcriptase inhibitor.

Other objects and advantages will become apparent to those skilled in the art from a review of the ensuing detailed description, which proceeds with reference to the following illustrative drawings, and the attendant claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows live-cell time lapse images of an HIV-1 infected H9 cell (upper) interacting with an uninfected GFP-MT2 target cell (lower), in co-culture. MitoTracker Red CMXRos stained mitochondria from the HIV-infected H9 cell are seen to enter the green GFP-MT2 target cell. A: Blue, Red, and Green overlay. B: Blue and Red overlay. Size bars 10 µm.

FIG. 2 shows live-cell real-time images of co-culture of HIV-1 infected H9 cells and uninfected GFP-MT2 target cells.

A: One hour post-mixing, showing infected H9 cells with red mitochondria and blue DNA, uninfected GFP-MT2 target cells in green, and newly infected target cells with yellow staining (MitoTracker Red on green). Various cellular structures, including nanotubes (NT, green arrow), filopodia, and infectious cell centers (ICCs) containing VS are seen around a large central syncytium (125×115 µm).

B: At hour 20, most of the target cells have been depleted. The original central syncytium has enlarged through the incorporation of the surrounding target cells and ICCs. Three new satellite syncytia are formed. MitoTracker Red stained red mitochondria increased significantly within the original syncytium. Release of cell-free mitochondria in culture is seen.

C: Transmission of red mitochondria (white arrows) from infected cells in an ICC via a nanotube (NT, green arrow) to the central syncytium, seen in a close up magnification of the area outlined by white dotted lines in 2A. Selected time lapse images are shown. Mitochondria migrate along the nanotubes at a rate of about 0.3 µm per minute.

D: Mitochondrial array: a new mode of mitochondrial movement and transfer. At hour 11, a mitochondrial array (MA) of MitoTracker Red-stained cell-free mitochondria emerges from one of the HIV-infected cells (blue arrow). Over a 30 minute period, this MA changed direction and navigated toward the syncytium. Selected time-lapse images from Movie 1 are shown.

Size bars in 2A and 2B, 25 µm, and in 2C and 2D, 10 µm.

FIG. 3 shows a typical field of GFP-MT2 target cells cultured in the presence of cell-free mitochondria purified from HIV-infected H9 cells.

A: One hour after mixing: green target cells are all clustered into ICC. Each ICC is attached to a tail-like structure made up of target cells infected with cell-free mitochondria.

B: The same field at hour 20: all target cells are infected and most of the green target cells are depleted. Release of cell-free mitochondria is seen.

C: Close up time-lapse images of white dotted area in FIG. 3A: at hour one, entry of cell-free mitochondria into an MT2 target cell results in accumulation of mitochondria (yellow-orange) at the site of entry. At hour 5 and 30 minutes, GFP expression diminishes in the target cell, and the newly infected cell shows red mitochondria and blue nuclear DNA.

Size bars in 3A and 3B, 25 µm, and in 3C, 10 µm.

FIG. 4 shows quantitation of HIV-1 spread by syncytia formation and p24 expression.

A: Syncytial formation. HIV-1 induced syncytia formation was measured in co-cultures of uninfected MT2 target cells with 1) uninfected H9 cells, 2) mitochondria purified from uninfected H9 cells, 3) HIV-1 infected H9 cells, 4) mitochondria purified from HIV-1 infected H9 cells, and 5) HIV-1 infected H9 cells treated with the mitochondria inhibitor CCCP. Syncytia formation was expressed as number per well. No syncytia were detected with uninfected H9 cells, or with purified cell-free mitochondria from uninfected cells. Syncytial formation was seen in co-cultures of MT2 cells with HIV-infected H9 cells, and with cell-free mitochondria purified from HIV-infected H9 cells. Treatment of HIV-infected H9 cells with 10 µM CCCP for 3 hours inhibited syncytia formation by 95%.

B: HIV-1 antigen p24 production. Viral antigen p24 production was measured in the supernatants of co-cultures as described above and expressed as ng/ml.

C: Live-cell fluorescent images of syncytial formation. GFP-MT2 target cells are green. H9 uninfected cells and HIV-1 infected H9 cells were fluorescently labeled with MitoTracker Red CMXRos to stain mitochondria red and Hoechst 33342 to stain DNA blue. Images shown are co-cultures of uninfected MT2 target cells with HIV-1 infected H9 cells (4C-1), uninfected H9 cells (4C-2), HIV-1 infected H9 cells treated with CCCP (4C-3), and mitochondria purified from HIV-1 infected H9 cells (4C-4). Syncytial formation was detected in co-cultures of MT2 cells with HIV-infected H9 cells, and with cell-free mitochondria purified from HIV-infected H9 cells. Treatment of HIV-infected H9 cells with CCCP blocked syncytia formation. No syncytia were detected with uninfected H9 cells, or with purified cell-free mitochondria from uninfected cells (not shown). Size bars 25 µm.

DETAILED DESCRIPTION OF THE INVENTION

HIV-1 is known to be disseminated via several distinct modes, including virological synapses (VS) [6, 7], syncytia [8], filopodial bridges [9], and nanotubes [10]. The present inventors hypothesized that formation of these structures would require metabolic energy and thus involve mitochondria. The precise roles of mitochondria during cell-to-cell spread of HIV-1 are unknown. As described herein, the present inventors used live-cell, real-time fluorescence imaging of co-cultures of HIV-1 infected T cells and uninfected target cells to examine the action of mitochondria during viral transmission. Findings presented herein demonstrate that mitochondria of HIV-1 infected cells enter uninfected target cells and promote cell-to-cell viral transmission. Moreover, cell-free mitochondria purified from HIV-infected cells are infectious and mitochondrial inhibitors inhibit cell-to-cell transmission of HIV-1. These findings show that mitochondria of HIV-1 infected cells play indispensable roles in cell-to-cell transmission of HIV and serve as viral reservoirs and carriers. Results presented herein thus offer new insights into the cellular mechanisms of viral transmission and suggest that mitochondria may be new targets for therapeutic intervention. The transfer of organelles between cells is a novel finding that has not been previously reported. Cell-to-cell transfer of mitochondria may be a general phenomenon, and its role in viral transmission may be only one of many implications. The role of mitochondria as a viral reservoir has implications for viral persistence and shielding from host immune responses.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A. Terminology

As used in this specification and the appended claims, the singular forms "a", "an", and "the" include plural references unless the context clearly dictates otherwise. Thus for example, reference to "the method" includes one or more methods, and/or steps of the type described herein and/or which will become apparent to those persons skilled in the art upon reading this disclosure.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

"Pharmaceutically acceptable vehicle" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates.

"Subject" means any animal or artificially modified animal. Animals include, but are not limited to, humans, non-human primates, cows, horses, sheep, goats, pigs, dogs, cats, rabbits, ferrets, rodents such as mice, rats and guinea pigs, and birds and fowl, such as chickens and turkeys. Artificially modified animals include, but are not limited to, transgenic animals or SCID mice with human immune systems. In the preferred embodiment, the subject is a human. Indeed, the terms "human," "patient" and "subject" can be used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. With respect HIV-1 infection, treatment may inhibit or decrease HIV-1 infection or cell-to-cell transmission thereof.

As used herein, the term "operably linked" refers to a regulatory sequence capable of mediating the expression of a coding sequence and which is placed in a DNA molecule (e.g., an expression vector) in an appropriate position relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

A "vector" is a replicon, such as a plasmid, cosmid, bacmid, phage or virus, to which another genetic sequence or element (either DNA or RNA) may be attached so as to bring about the replication of the attached sequence or element.

An "expression vector" or "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The terms "transform", "transfect", or "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. In other applications, the introduced nucleic acid may exist in the recipient cell or host organism only transiently.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the basic and novel characteristics of the sequence.

The term "isolated" refers to the state in which specific binding members of the invention, or nucleic acid encoding such binding members will be, in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practiced in vitro or in vivo. Members and nucleic acid may be formulated with diluents or adjuvants and still for practical purposes be isolated—for example the members will normally be mixed with gelatin or other carriers if used to coat microtiter plates for use in immunoassays, or will be mixed with pharmaceutically acceptable carriers or diluents when used in diagnosis or therapy.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease Si), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to probes of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

Primers may be labeled fluorescently with 6-carboxyfluorescein (6-FAM). Alternatively primers may be labeled with 4,7,2',7'-Tetrachloro-6-carboxyfluorescein (TET). Other alternative DNA labeling methods are known in the art and are contemplated to be within the scope of the invention.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like). "Mature protein" or "mature polypeptide" shall mean a polypeptide possessing the sequence of the polypeptide after any processing events that normally occur to the polypeptide during the course of its genesis, such as proteolytic processing from a polypeptide precursor. In designating the sequence or boundaries of a mature protein, the first amino acid of the mature protein sequence is designated as amino acid residue 1.

The term "tag", "tag sequence" or "protein tag" refers to a chemical moiety, either a nucleotide, oligonucleotide, polynucleotide or an amino acid, peptide or protein or other chemical, that when added to another sequence, provides additional utility or confers useful properties to the sequence, particularly with regard to methods relating to the detection or isolation of the sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by, the trained artisan, and are contemplated to be within the scope of this definition.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

As used herein, an "agent", "candidate compound", or "test compound" may be used to refer to, for example, nucleic acids (e.g., DNA and RNA), carbohydrates, lipids, proteins, peptides, peptidomimetics, small molecules and other drugs. In particular the term agent includes compounds such as test compounds or drug candidate compounds.

The term "control substance", "control agent", or "control compound" as used herein refers a molecule that is inert or has no activity relating to an ability to modulate a biological activity. With respect to the present disclosure, such control substances are inert with respect to an ability to modulate mitochondrial activity. Exemplary controls include, but are not limited to, solutions comprising physiological salt concentrations.

The term 'agonist' refers to a ligand that stimulates the receptor the ligand binds to in the broadest sense or stimulates a response that would be elicited on binding of a natural binder to a binding site.

The term 'assay' means any process used to measure a specific property of a compound or agent. A 'screening assay' means a process used to characterize or select compounds based upon their activity from a collection of compounds.

As used herein, "pg" means picogram, "ng" means nanogram, "ug" or "µg" mean microgram, "mg" means milligram, "ul" or "µl" mean microliter, "ml" means milliliter, "l" means liter.

The compositions containing the molecules, compounds, or agents described herein can be administered for therapeutic purposes. In therapeutic applications, compositions are administered to a patient already suffering from an HIV-1 infection (such as, e.g., an AIDS patient) in an amount sufficient to at least partially arrest the symptoms of the disease and its complications. An amount adequate to accomplish this is defined as a "therapeutically effective amount or dose." Amounts effective for this use will depend on the severity of the disease and the weight and general state of the patient.

"Infection", as the term is used herein, generally relates to the entry, replication, insertion, lysis or other event or process involved in the pathogenesis of a virus with respect to a host cell. Thus, decreasing infection includes decreasing entry, replication, insertion, lysis, cell-to-cell transmission, or other pathogenic process of a virus in a cell or subject, or combinations thereof. Infection includes the introduction of an infectious agent, such as a non-recombinant virus, recombinant virus, plasmid, or other agent capable of infecting a host, such as the cell of a subject.

"Exposed" to HIV-1 means contact or association with HIV-1 such that infection could result.

"HIV-1 infected" means the introduction of viral components, virus particles, or viral genetic information into a cell, such as by fusion of the cell membrane with HIV-1. The cell may be a cell of a subject. In the preferred embodiment, the cell is a cell in a human subject.

B. Detailed Disclosure

The invention relates generally to methods and agents for inhibiting mitochondrial mediated transmission of HIV-1. Prior to the present discoveries, the role of mitochondria in the cell-to-cell transmission of HIV-1 was unappreciated. The discovery that mitochondria play a critical role in cell-to-cell transmission of HIV-1 provides for novel methods for treating HIV-1 disease using mitochondrial inhibitors, either alone or in conjunction with known anti-HIV-1 therapeutic agents and regimens, and assays for screening and identifying agents, compounds or peptides to modulate mitochondrial activity that may be used to identify novel therapeutics for treating AIDS patients.

Further to the above, the present inventors demonstrate herein that functional mitochondria are essential for cell-to-cell transmission of the virus by, for example, pre-treating HIV-1 infected H9 cells with mitochondrial inhibitors including carbonyl cyanide m-chlorophenylhydrazone (CCCP, 10 µM), antimycin A (2.4 µM), and oligomycin (2.4 µM) for 3 hours and evaluating the effect of these inhibitors on cell-tocell viral HIV-1 transmission. The concentrations used for the indicated inhibitors conferred maximum inhibition of the targeted metabolic step, but caused no cell death. After pre-treatment, cells were washed to remove free drug, suspended in complete medium, and labeled with MitoTracker Red and Hoechst 33342. Pre-treated cells were then co-cultured with GFP-MT2 target cells, and cell-to-cell transmission of HIV-1 was analyzed. As shown in FIG. 4C-3, mitochondrial inhibitors reduced cell-to-cell spread of HIV-1 and decreased VS and syncytia formation. Accordingly, mitochondrial inhibitors are useful compounds/agents for inhibiting HIV-1 cell-to-cell transmission. In light of these findings, methods are presented herein to screen known mitochondrial inhibitors to evaluate their ability to inhibit viral (e.g., HIV-1) cell-to-cell transmission and to identify new mitochondrial inhibitors that can be used in methods to inhibit viral (e.g., HIV-1) cell-to-cell transmission.

In vivo animal models of HIV-1 or HIV-1-like viral infection or HIV-1 immune response may be utilized by the skilled artisan to further or additionally screen, assess, and/or verify mitochondrial inhibitors, or agents identified using screening methods of the present invention, as useful for treating HIV-1 infected subjects in vivo. Such animal models include, but are not limited to models of immune system modulation or immune response. In particular, HIV models, including "humanized" mice models are known and can be utilized. Immunodeficient mice are engrafted with a human immune system using various sources of hematopoietic stem cells, depending on the model (CD34+ cells from fetal liver, from cord blood, etc). Humanized mice such as, for example, humanized bone marrow-liver-thymus (BLT) mice (Wege A K et al 92008) Curr Top Microbiol Immunol 324:149-165; Denton P W et al (2008) PLoS January 15; 5(1):e16) may be challenged with HIV-1 after immunization. DKO-hu HSC mice may also be used as a humanized mouse model susceptible to HIV infection (Zhang L et al (2007) Blood 109(7): 2978-81). Hu-PBL-SCID mice have, moreover, been immunized with IFN-DCs and pulsed with inactivated HIV-1 or infected with HIV-1 to assess response and protection (Lapenta C et al (2003) J Exp Med 198(2):361-7).

Mitochondrial inhibitors or agents identified using screening methods of the present invention may be administered to a patient in need of treatment via any suitable route, including by intravenous, intraperitoneal, intramuscular injection, or orally.

Mitochondrial Inhibitors

Exemplary mitochondrial inhibitors of the invention, include, without limitation: carbonyl cyanide m-chlorophenyl hydrazone (CCCP; $H^+$ ionophore), antimycin A and myxothiazol (inhibitors of complex III), oligomycin, and rotenone (inhibitor of complex I). CCCP is a chemical inhibitor of oxidative phosphorylation. It is a nitrile, hydrazone and ionophore. CCCP affects protein synthesis reactions in mitochondria. CCCP causes an uncoupling of the proton gradient that is established during the normal activity of electron carriers in the electron transport chain. CCCP behaves predominantly as an ionophore and reduces the ability of ATP synthase to function optimally.

Antimycin A binds to the Qi site of cytochrome c reductase, thereby inhibiting the oxidation of ubiquinol in the electron transport chain of oxidative phosphorylation. The inhibition of this reaction disrupts the formation of the proton gradient across the inner membrane. The production of ATP is subsequently inhibited, as protons are unable to flow through the ATP synthase complex in the absence of a proton gradient. This inhibition also results in the formation of quantities of the toxic free radical superoxide.

Oligomycin inhibits ATP synthase by blocking its proton channel, which is necessary for oxidative phosphorylation of ADP to ATP (energy production). The inhibition of ATP synthesis also inhibits the electron transport chain. Because the high proton concentration build up is not dissipated, the free energy released by biological oxidation of substrates is not enough to pump any more protons against the steep gradient. A potential complication of administering oligomycin to an individual is the accumulation of high levels of lactate in the blood and urine. Such potentialities would have to be monitored diligently and measures taken to correct for elevated levels of lactate in any individual treated with oligomycin. Oligomycin is also an inhibitor of ATP synthase. In oxidative phosphorylation research, it is used to prevent state 3 (phosphorylating) respiration. Oligomycin also has utility as an antibiotic.

Mitochondrial inhibitors, such as those proposed for the treatment of certain cancers are also encompassed herein. Such mitochondrial inhibitors include, without limitation, efrapeptin F, which is a mitochondrial complex V inhibitor, and inhibitors of complex I, II, III, and other inhibitors of complex V. Such mitochondrial inhibitors show preferential cytotoxicity to human pancreatic cancer PANC-1 cells under glucose-deprived conditions. See Momose et al. (Biochem. Biophys. Res. Comm. 392:460-466, 2010), the entire of contents of which is incorporated herein in its entirety. Mitochondrial inhibitors and uses thereof are, moreover, described in Galluzzi et al. (Oncogene 25:4812-4830, 2006) and these inhibitors and guidance relating to their use is applicable to the treatment of patients afflicted with HIV-1. The entire content of Galluzzi et al. (Oncogene 25:4812-4830, 2006) is incorporated herein in its entirety.

Also encompassed herein are the mitochondrial inhibitors NV-128 and ME-344 and uses thereof for treating patients afflicted with HIV-1. NV-128, for example, has demonstrated activity against a broad range of cancers I pre-clinical studies. NV-128 treatment of cancer cells induces a rapid loss of cellular energy resulting in the inhibition of both mammalian target of rapamycin (mTOR1 and mTOR2) pathways. Pre-clinical studies using NV-128 reveal that it induces mitochondrial instability that ultimately leads to cell death in otherwise chemotherapy-resistant ovarian cancer stem cells. See, for example, Alvero et al. Cancer 115: 3204-3216, 2009; Alvero et al. Mol Cancer Ther 10:1385-1393, 2011.

ME-344 is an active metabolite of NV-128 that exhibits superior anti-tumor activity against a broad spectrum of human cancer cell lines relative to that of NV-128 in pre-clinical studies. A Phase I clinical trial of intravenously administered ME-344 in patients with solid refractory tumors is ongoing. The protocol calls for five escalating dose cohorts to evaluate safety and tolerability of intravenous (iv) ME-344. The trial is also designed to characterize the pharmacokinetic profile of ME-344 and reveal any preliminary clinical anti-tumor activity. Intravenous infusions of ME-344 are administered once weekly for three weeks and may optionally, continue with weekly dosing pending safety assessment and evidence of clinical benefit. With regard to ME-344, the content of European Patent No. 1 794 141 is incorporated herein by reference in its entirety.

The IUPAC/chemical name of ME-344 is 4,4'-7-hydroxy-8-methylchroman-3,4-diyl)diphenol. The chemical structure of ME-344 is as follows:

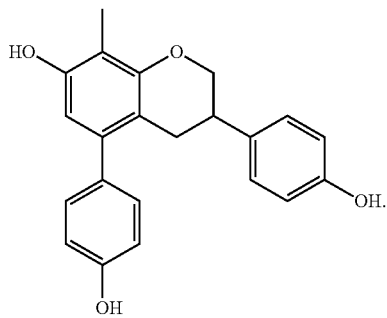 [SMILES: Cc1c(O)cc(-c2ccc(O)cc2)c2c1OCC(c1ccc(O)cc1)C2]

In another embodiment, the mitochondrial inhibitor is dichloroacetate (DCA), an inhibitor of mitochondrial pyruvate dehydrogenase kinase. DCA has been evaluated in clinical trials for the treatment of malignant glioma and glioblastome multiforme. DCA is administered orally and is a small molecule that readily crosses the blood brain barrier to access HIV-1 infected cells in the brain. Additional information pertaining to, for example, dosing parameters used in the Phase II Clinical study directed to the above can be found via the formal title: "A Phase II Open-labeled, Double-arm Clinical Study of Dichloroacetate (DCA) in Malignant Gliomas and Glioblastome (GMB) Patients" as presented in publicly available web sites directed to clinical trials and provided as a service by the U.S. National Institutes of Health.

In a further embodiment, a mitochondrial inhibitor may also exhibit proteosome inhibitor activity. An exemplary such mitochondrial and proteosome inhibitor is bortezomib. This compound has been evaluated in Phase I, II, and II clinical trials. See, for example, Ling et al. (J Biol Chem 278:33714-33723, 2003) and references cited therein, the entire content of each of which is incorporated herein by reference.

Methods of Screening to Identify Inhibitors of Mitochondrial Mediated HIV-1 Transmission Suitable screening methods are set forth in the Examples presented herein. As described herein, a suitable source of HIV-1 virus, such as H9 cells infected with HIV-1, or an isolate of purified HIV-1 (HIV-IIIB), and target cells that are susceptible to HIV-1 infection, such as MT2 cells, are co-cultured to achieve infection. Infected cells and target cells can be differentially labeled using, for example, a fluorescent label [e.g., MitoTracker Red CMXRos and green fluorescent protein (GFP-MT2)] to differentiate the cellular origin of organelles visualized in co-cultures thereof. Live-cell real-time images and time lapse movies can be used to visualize HIV-1 infection and transmission. Syncytia formation assays can also be used to assess acute HIV-1 infection. Viral replication can also be assayed by measuring HIV-1 core protein p24 expression in the co-culture. HIV-1 core protein p24 expression may be assayed using a variety of means including commercially available ELISA kits. Syncytia formation assays and HIV-1 core protein p24 expression assays are described in detail in Lee-Huang et al., Structural and Functional Modeling of Human Lysozyme Reveals a Unique Nonapeptide, HL9, with Anti-HIV Activity. Biochemistry 44 (2005) 4648-4655, the entire contents of which is incorporated herein in its entirety.

Other suitable target cells, which are susceptible to HIV-1 infection, are known in the art and include, without limitation, any CD4 positive T cells or other types of cells, including monocytes, primary cells, and body fluids comprising target cells.

With regard to potential sources of HIV-1, any isolates and/or body fluids derived from AIDS patients or HIV-1 positive subjects, as well as other laboratory strains may be utilized.

Individual compounds or libraries of compounds can be screened using any one or all of the above assays to determine if the presence of the compound in the co-culture reduces mitochondrial mediated cell-to-cell transmission of HIV-1 relative to co-cultures incubated in the presence of control compound.

PHARMACEUTICAL COMPOSITIONS

When employed as pharmaceuticals, mitochondrial inhibitors or agents identified using screening methods of the present invention are typically administered in the form of a pharmaceutical composition. Such compositions can be prepared in a manner well known in the pharmaceutical art and comprise at least one active compound.

Generally, mitochondrial inhibitors or agents of this invention are administered in a pharmaceutically effective amount. The amount of the mitochondrial inhibitor or agent actually administered will typically be determined by a physician, in the light of the relevant circumstances, including the condition to be treated, the chosen route of administration, the actual compound-administered, the age, weight, and response of the individual patient, the severity of the patient's symptoms, and the like.

The mitochondrial inhibitors or agents identified using screening methods of the present invention may be used alone or in combination with other therapeutic agents used for treating subjects infected with HIV-1. Accordingly, pharmaceutical compositions may comprise one or more mitochondrial inhibitors or agents identified using screening methods of the present invention and such compositions may further comprise one or more other therapeutic agents used for treating subjects infected with HIV-1. Such therapeutic agents include: nucleoside analogue reverse transcriptase inhibitors and either of protease inhibitors or non-nucleoside reverse transcriptase inhibitors. For such a combined therapeutic approach, compositions may comprise all of the above or multiple compositions may be formulated and administered to a subject in need thereof, concomitantly or at appropriately space intervals for optimal therapeutic efficacy.

Examples of nucleoside analogue reverse transcriptase inhibitors (NRTIs) include: Abacavir (Ziagen), and the combination of drugs emtricitabine and tenofovir (Truvada) and lamivudine and zidovudine (Combivir). Examples of protease inhibitors include: atazanavir (Revataz), darunavir (Prezista), fosamprenavir (Lexiva), and ritonavir (Norvir). Examples of non-nucleoside reverse transcriptase inhibitors (NNRTIs) include: efavirenz (Sustiva), etravirine (Intelence), and nevirapine (Viramune).

Other agents used for the treatment of subjects infected with HIV-1 include entry or fusion inhibitors, including enfuvirtide (Fuzeon) and maraviroc (Selzentry), and integrase inhibitors, such as raltegravir (Isentress).

The pharmaceutical compositions of this invention can be administered by a variety of routes including oral, rectal, transdermal, subcutaneous, intravenous, intramuscular, and intranasal. Depending on the intended route of delivery, the mitochondrial inhibitors or agents of this invention are preferably formulated as either injectable or oral compositions or as salves, as lotions or as patches all for transdermal administration.

The compositions for oral administration can take the form of bulk liquid solutions or suspensions, or bulk powders.

More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences*, 17th edition, 1985, Mack Publishing Company, Easton, Pa., which is incorporated herein by reference.

The mitochondrial inhibitors or agents of this invention (i.e., compounds) can also be administered in sustained release forms or from sustained release drug delivery systems. A description of representative sustained release materials can be found in *Remingtons's Pharmaceutical Sciences*.

The following formulation examples illustrate representative pharmaceutical compositions of this invention. The present invention, however, is not limited to the following pharmaceutical compositions.

Formulation 1

Tablets

A compound of the invention is admixed as a dry powder with a dry gelatin binder in an approximate 1:2 weight ratio. A minor amount of magnesium stearate is added as a lubricant. The mixture is formed into 240-270 mg tablets (80-90 mg of active amide compound per tablet) in a tablet press.

Formulation 2

Capsules

A compound of the invention is admixed as a dry powder with a starch diluent in an approximate 1:1 weight ratio. The mixture is filled into 250 mg capsules (125 mg of active amide compound per capsule).

Formulation 3

Liquid

A compound of the invention (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4

Tablets

A compound of the invention is admixed as a dry powder with a dry gelatin binder in an approximate 1:2 weight ratio. A minor amount of magnesium stearate is added as a lubricant. The mixture is formed into 450-900 mg tablets (150-300 mg of active amide compound) in a tablet press.

Formulation 5

Injection

A compound of the invention is dissolved or suspended in a buffered sterile saline injectable aqueous medium to a concentration of approximately 5 mg/ml.

Formulation 6

Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present compounds are used as therapeutic agents for the treatment of conditions in mammals that are causally related or attributable to HIV-1 infection. Accordingly, the compounds and pharmaceutical compositions of this invention find use as therapeutics for preventing and/or treating diseases causally related or attributable to HIV-1 infection, including AIDS, in mammals. In a particular embodiment, the mammal is a human.

In a method of treatment aspect, this invention provides a method of treating a mammal susceptible to or afflicted with a condition associated with an HIV-1 infection, which method comprises administering an effective amount of one or more of the pharmaceutical compositions just described.

As a further aspect of the invention there is provided the present compounds for use as a pharmaceutical especially in the treatment or prevention of the aforementioned conditions and diseases. Also provided herein is the use of the present compounds in the manufacture of a medicament for the treatment or prevention of one of the aforementioned conditions and diseases.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as, e.g., AIDS and AIDS-related diseases, the regimen for treatment usually stretches over many months or years, so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound of the invention, with preferred doses each providing from about 0.1 to about 10 mg/kg and especially about 1 to about 5 mg/kg.

Transdermal doses are generally selected to provide similar or lower blood levels than are achieved using injection doses. Modes of administration suitable for mucosal sites are also envisioned herein and include without limitation: intra-anal swabs, enemas, intranasal sprays, and aerosolized or vaporized compounds and/or compositions for delivery to the lung mucosa. One of skill in the art would choose an appropriate delivery mode/s based on a variety of parameters, including the organ or tissue site in a patient with a disease or condition that is most severely affected by the disease or condition.

The compounds of this invention can be administered as the sole active agent or they can be administered in combination with other agents, including other compounds that demonstrate the same or a similar therapeutic activity and are determined to safe and efficacious for such combined administration.

As described herein, mitochondrial inhibitors or agents identified using screening methods of the present invention may be used alone or in combination with other therapeutic agents used for treating subjects infected with HIV-1. Accordingly, one or more mitochondrial inhibitors or agents identified using screening methods of the present invention may be administered alone or in conjunction with one or more other therapeutic agents used for treating subjects infected with HIV-1. Such therapeutic agents include: nucleoside analogue reverse transcriptase inhibitors and either of protease inhibitors or non-nucleoside reverse transcriptase inhibitors, HIV-1 entry or fusion inhibitors, and integrase inhibitors. For such a combined therapeutic approach, one or more mitochondrial inhibitors or agents identified using screening methods of the present invention may be administered to patient in need thereof concomitantly with one or more other therapeutic agents used for treating subjects infected with HIV-1, such as NRTIs, protease inhibitors, and/or NNRTIs, or may be administered in a therapeutic regimen at appropriately space intervals to achieve optimal therapeutic efficacy.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLES

Materials and Methods

Cell Lines and Viruses.

HIV-1 infected H9 cells, MT2 target cells, and HIV-IIIB were obtained through the AIDS Research and Reference Program, Division of AIDS, National Institute of Allergy and Infectious Diseases, National Institutes of Health. HIV-IIIB and HIV-IIIB infected H9 cells were originally from R. Gallo [11]. MT2 cells were originally from D. Richman [12].

Cell Labeling and Co-Culture.

HIV-1 infected H9 cells were fluorescently labeled with MitoTracker Red CMXRos to stain mitochondria red, and with Hoechst 33342 to stain DNA blue according to the manufacturer's protocols (Molecular Probes). Uninfected MT2 target cells were labeled green by the expression of green fluorescent protein (GFP-MT2). Cells were co-cultured and imaged on a glass bottom 96-well plate (MatTek, Ashland, Mass.) in RPMI 1640 medium containing 10% heat-inactivated fetal calf serum, 2 mM L-glutamine, 100 U/ml penicillin and 100 µg/ml streptomycin (complete medium). Labeled HIV-1 infected H9 cells were washed 3 times with complete medium to remove any residual free virus and free dye. Washed cells were suspended in complete medium at a density of $5 \times 10^5$ cells/ml. 100 µl of this cell suspension, containing 50,000 cells, were plated into each well. 100,000 GFP-MT2 target cells in 100 µl were then added to each well, to give a ratio of 1:2 of infected to uninfected target cells.

Live-Cell Real-Time Imaging.

Live-cell real-time images and time lapse movies were collected at 37° C., 5% $CO_2$ using a microplate incubator, with precision temperature, humidity and $CO_2$ controls, mounted on the microscope stage of a Leica inverted microscope equipped with an automatic power stage and an AF6000 camera. Phase contrast, blue (Hoechst 33342), green (GFP), and red (MitoTracker) channels were used for imaging. Images were collected at 0.5 min or 5 min intervals for 18-24 hours. Image analysis was performed using LCSAF software.

Syncytia Formation Assay.

Acute HIV infection of the target cells as a result of cell-to-cell transmission of the virus was measured by syncytia formation assay [13]. Focal syncytium formation was scored under an inverted microscope.

HIV-1 p24 Assay.

Viral replication was assayed by HIV-1 core protein p24 expression in the co-culture, using commercial ELISA kit (Coulter, Hialeah, Fla.) as described previously [13].

Data Analysis and Statistics.

For quantitation of syncytial formation and HIV p24 production, data are means±standard deviations of four independent experiments. Experiments were carried out in triplicates in each run. For live-cell real-time imaging and movies, independent experiments were repeated at least four times and each time in triplicates.

Results

Mitochondria of HIV Infected Cells Enter Uninfected Target Cells Upon Contact

FIG. 1 shows that upon contact, mitochondria from an infected H9 cell, stained with MitoTracker Red, enter an uninfected GFP-MT2 target cell. Mitochondrial entry can be followed by location and intensity of staining. In the blue-red-green overlay (FIG. 1A), mitochondria entering the target cell are seen as yellow spots progressing from the cell-to-cell contact zone to the interior of the target cell. As more mitochondria enter the target cell, the intensity of the yellow in the green target cell increases with time. In the absence of the green overlay (FIG. 1B), the mitochondria from the HIV-1 infected H9 cell can be explicitly seen as red stained structures inside the target cell.

Mitochondria of HIV Infected Cells Carry the Virus into the Target Cells; Viral Infection Induces Vs and Syncytia Formation and Target Cell Depletion FIG. 2 shows one field of the co-culture at hour 1 (FIG. 2A) and hour 20 (FIG. 2B) after mixing in Movie 1 (video 1). At hour 1, various infectious cell centers (ICC) are formed, consisting of target cells (green), HIV infected H9 cells (red and blue) and partially infected target cells (red in green appearing as orange and yellow). These ICCs, including VS, nanotubes, and filopodia, are seen around a large central syncytium, 125×115 p.m. By hour 20, most of the target cells have been depleted, and new satellite syncytia have formed around the original central syncytium. MitoTracker-stained red mitochondria, both within the syncytium and free in culture, are seen.

Mitochondria can be Transported at a Distance by Nanotubes

Closer examination of one region of interest, outlined by the dotted lines in FIG. 2A, shows the presence of a 25×5 μm nanotube (NT) linking the ICC to the syncytium. Detailed analysis of time lapse images every 5 minutes shows that discrete groups of MitoTracker-stained mitochondria (white arrows) migrate along the nanotube from the infected cells into the syncytium at a rate of about 0.3 μm per minute. Selected frames are shown in FIG. 2C. As the mitochondria reach the syncytium, the size and intensity of MitoTracker staining at the surface and interior of the syncytium increase.

Mitochondria can be Transported at a Distance in Groups as an Array

Mitochondria can also be transmitted from HIV infected cells to uninfected cells as a mitochondrial array (MA). This is a new mode of mitochondrial release and movement that we observed in the co-culture. FIG. 2D shows the same field shown in FIG. 2C at hour 11. An array of cell-free mitochondria stained with MitoTracker Red is seen to emerge from one of the infected cells (blue arrow). Over a 30 minute period, this mitochondrial array changed direction and navigated toward the syncytium at a rate of about 0.3 μm per minute (video 1 and FIG. 2D). We observed this type of free mitochondrial array many times in the co-cultures.

Cell-Free Mitochondria Purified from HIV Infected Cells are Infectious

Because mitochondrial transfer from infected cells to uninfected target cells was observed concurrent with viral spread, the present inventors tested whether highly purified cell-free mitochondria from HIV-infected cells are infectious. To this end, mitochondria from HIV-infected H9 cells were isolated and purified to remove cellular and viral contaminants, including free virus. Their infectivity was evaluated by adding them to uninfected GFP-MT2 target cells. In the experiment shown, the only intact cells present are uninfected (green) GFP-MT2 target cells. HIV-infected cells were stained with MitoTracker Red and Hoechst prior to mitochondrial isolation, so as to visualize mitochondria derived therefrom in co-cultures. Live-cell real-time images are shown in FIG. 3. The results presented herein demonstrate that highly purified cell-free mitochondria from HIV-1 infected H9 cells are infectious. They harbor the virus and carry the virus into the target cells, infect them, and promote HIV-induced cytopathologic effects on the target cells. The present inventors confirmed viral infection and replication by syncytia formation and HIV antigen p24 production (FIG. 4).

Mitochondria from HIV-Infected Cells Invade Target Cells; Viral Infection and Replication Promote Target Cell Depletion FIG. 3A represents a typical field of GFP-labeled MT2 target cells in the presence of cell-free mitochondria purified from HIV-infected H9 cells, one hour after mixing. At this point, green target cells are all clustered with infectious mitochondria into ICCs. FIG. 3B represents the same field at hour 20. By this time, the entire field of target cells has been infected, most of them are depleted, and release of free mitochondria can be seen. These second generation cell-free mitochondria are as infectious as the original mitochondria. To examine the mechanism of cell-free mitochondria in HIV transmission, frame-by-frame analysis was performed. As seen in FIG. 3C, entry of free mitochondria into a GFP-MT2 target cell results in accumulation of mitochondria (colored yellow in the red-green-blue overlay) near the site of entry. Viral replication promotes depletion of the target cell and diminishes its GFP expression. Finally, at hour 5 and 30 minutes, GFP expression is no longer visible, but the now infected cell is seen with red mitochondria and blue nuclear DNA.

Mitochondrial Inhibitors Block HIV Transmission

To verify that functional mitochondria are essential for cell-to-cell transmission of the virus, we pre-treated HIV-1 infected H9 cells with mitochondrial inhibitors including carbonyl cyanide m-chlorophenylhydrazone (CCCP, 10 μM), antimycin A (2.4 μM), and oligomycin (2.4 μM) for 3 hours [14]. These concentrations gave maximum inhibition of the targeted metabolic step and caused no cell death. Cells were washed three times to remove free drug, then suspended in complete medium, and labeled with MitoTracker Red and Hoechst 33342. The cells were then co-cultured with GFP-MT2 target cells, and cell-to-cell transmission of HIV-1 was analyzed. Mitochondrial inhibitors reduced cell-to-cell spread of HIV-1 and decreased VS and syncytia formation (FIG. 4C-3).

Confirmation of Mitochondria as HIV Reservoirs and Carriers

To confirm that mitochondria from HIV infected cells serve as viral reservoirs and carry the virus into the uninfected target cells, the present inventors quantitated viral infection and replication in the co-cultures by syncytia formation and viral antigen p24 production. These results are seen in FIG. 4. This was achieved using co-cultures of uninfected MT2 target cells with 1) uninfected H9 cells as controls, 2) cell-free mitochondria purified from uninfected H9 cells, 3) HIV-infected H9 cells, 4) cell-free mitochondria purified from infected H9 cells, and 5) HIV-infected H9 cells treated with the mitochondrial inhibitor CCCP. As shown in FIGS. 4A and 4B, syncytial formation and p24 production were detected in co-cultures of MT2 cells with HIV-infected H9 cells, as well as with cell-free mitochondria purified from HIV-infected H9 cells. No syncytia were found with uninfected H9 cells, or with purified cell-free mitochondria from uninfected cells, nor was there p24 production. Treatment of HIV-infected H9 cells with CCCP reduced syncytia formation and p24 expression by about 95%. FIG. 4C contains fluorescent images showing syncytia formation in co-cultures of GFP-MT2 target cells with HIV-1 infected H9 cells (FIG. 4C-1) but not with uninfected H9 cells (FIG. 4C-2). CCCP-treatment of HIV-1 infected H9 cells inhibits syncytia formation (FIG. 4C-3) while cell-free mitochondria from HIV-1 infected H9 cells promote syncytia formation (FIG. 4C-4).

Discussion

The present inventors used live-cell real-time imaging to follow mitochondria stained with MitoTracker Red CMXRos in HIV-1 infected H9 cells, in co-culture with uninfected GFP-MT2 target cells. This dye is retained by active mitochondria, and depends on the presence of the mitochondrial membrane potential. As described herein, the present inventors discovered that host mitochondria act as viral reservoirs, and carry the virus into the target cells, facilitating viral transmission. Furthermore, purified cell-free mitochondria from HIV-1 infected cells are capable of infecting target cells and forming ICCs consisting of VS and syncytia. In agreement with these findings, pre-treatment of infected cells with mitochondrial inhibitors reduced viral transmission. The present inventors confirmed viral transmission, target cell infection and viral replication by syncytial formation and HIV core protein p24 production. Co-cultures of uninfected H9 cells, similarly stained with Hoechst and Mito-Tracker Red, with uninfected GFP-MT2 target cells failed to show ICC and syncytial formation, nor did they show viral replication or HIV-p24 production.

Overall, results presented herein show that mitochondria of HIV-infected cells play indispensable roles in cell-to-cell transmission of HIV-1. They suggest that mitochondria act as reservoirs and carriers for HIV-1. How the AIDS virus acts on the host mitochondria and where it hides in the mitochondria are fascinating questions. The size of HIV-1 is about 0.1 μm and that of a mitochondrion is between 1 to 10 μm, so there should be ample space for the virus. The number of mitochondria per cell varies with cell type and metabolic state, and could spike to 1000-2000. Mitochondria are dynamic organelles that undergo rapid cycles of fusion and fission to maintain cellular physiology and function. All of these may be useful to the virus for rapid dissemination, in addition to shielding the virus from cellular and immunological barriers.

Membrane fusion is a fundamental process in human life in health and in disease. Transport vesicles fuse with the organelles of the secretory pathway, gametes fuse during fertilization, and enveloped viruses fuse with receptors of the target cells during entry. The fusion mechanism for these diverse events may be different, but they may operate by some common strategies. How HIV interacts with the host mitochondria is an important and as yet unstudied area. Does the viral fusion protein gp41 [15] interact with the mitochondria fusion proteins [16]? Mitochondria are double membrane-bound organelles. Are both membranes involved in the fusion with the virus?

Results presented herein demonstrate for the first time the essential role of mitochondria in cell-to-cell transmission of HIV-1, and reveal that mitochondria and mitochondrial comprising HIV-1 can be transferred between cells.

REFERENCES

[1] Q. Sattentau, Avoiding the void: cell-to-cell spread of human viruses. Nat Rev Microbiol 6 (2008) 815-826.

[2] H. Sato, J. Orenstein, D. Dimitrov, and M. Martin, Cell-cell spread of HIV-1 occurs within minutes and may not involve the participation of virus particles. Virology 186 (1992) 712-724.

[3] D. S. Dimitrov, R. L. Willey, H. Sato, L. J. Chang, R. Blumenthal, and M. A. Martin, Quantitation of human immunodeficiency virus type 1 infection kinetics. J Virol 67 (1993) 2182-2190.

[4] M. Sourisseau, N. Sol-Foulon, F. Porrot, F. Blanchet, and O, Schwartz, Inefficient human immunodeficiency virus replication in mobile lymphocytes. J Virol 81 (2007) 1000-1012.

[5] P. Chen, W. Hubner, M. A. Spinelli and B. K. Chen, Predominant mode of human immunodeficiency virus transfer between T cells is mediated by sustained Env-dependent neutralization-resistant virological synapses. J Virol 81 (2007) 12582-12595.

[6] D. Rudnicka, J. Feldmann, F. Porrot, S. Wietgrefe, S. Guadagnini, M. C. Prevost, J. Estaquier, A. T. Haase, N. Sol-Foulon, and O, Schwartz, Simultaneous cell-to-cell transmission of human immunodeficiency virus to multiple targets through polysynapses. J Virol 83 (2009) 6234-6246.

[7] W. Hübner, G. P. McNerney, P. Chen, B. M. Dale, R. E. Gordon, F. Y. Chuang, X. D. Li, D. M. Asmuth, T. Huser, B. K. Chen, Quantitative 3D video microscopy of HIV transfer across T cell virological synapses. Science 323 (2009) 1743-1747.

[8] B. A. Watkins, R. Crowley, A. E. Davis, A. T. Louie, and M. S. Reitz, Syncytium formation induced by human immunodeficiency virus type 1 isolates correlates with affinity for CD4. J Gen Virol 78 (1997) 2513-2522.

[9] N. M. Sherer, M. J. Lehmann, L. F. Jimenez-Soto, C. Horensavitz, M. Pypaert, and W. Mothes, Retroviruses can establish filopodial bridges for efficient cell-to-cell transmission. Nat Cell Biol 9 (2007) 310-315.

[10] E. A. Eugenin, P. J. Gaskill, and J. W. Berman, Tunneling nanotubes (TNT) are induced by HIV-infection of macrophages: A potential mechanism for intercellular HIV trafficking. Cell Immunol 254 (2009) 142-148.

[11] D. L. Mann, S. J. O'Brien, D. A. Gilbert, Y. Reid, M. Popovic, E. Read-Connole, R. Gallo, A. Gazdar, Origin of the HIV-susceptible human CD4+ cell line H9, AIDS Res. Hum. Retroviruses 5 (1989) 253-255.

[12] S. Harada, Y. Koyanagi, N. Yamamoto, Infection of HTLV-III/LAV in HTLV-I carrying cells MT-2 and MT-4 and application in a plaque assay. Science 229 (1985) 563-566.

[13] S. Lee-Huang, V. Maiorov, P. Lin Huang, H. C. Lee, A. Ng, Y-T. Chang, N. Kallenbach, P. Lee Huang, and H-C. Chen, Structural and Functional Modeling of Human Lysozyme Reveals a Unique Nonapeptide, HL9, with Anti-HIV Activity. Biochemistry 44 (2005) 4648-4655.

[14] O. Guillery, F. Malka, P. Frachon, D. Milea, M. Rojo, A. Lombes, Modulation of mitochondrial morphology by bioenergetics defects in primary human fibroblasts. Neuromuscul Disord 18 (2008) 319-330.

[15] S. Lee-Huang, P. Lin Huang, D. Zhang, J. W. Lee, J. Bao, Y. T. Sun, Y-T. Chang, J. Zhang and P. Lee Huang. Discovery of small-molecule HIV-1 fusion and integrase inhibitors oleuropein and hydroxytyrosol: Part I. Fusion inhibition. Biochemical and Biophysical Research Communications, 354 (2007) 872-878.

[16] S. Meeusen, J. M. McCaffery and J. Nunnari, Mitochondrial fusion intermediates revealed in vitro. Science 305 (2004) 1747-1752

This invention may be embodied in other forms or carried out in other ways without departing from the spirit or essential characteristics thereof. The present disclosure is therefore to be considered as in all aspects illustrate and not restrictive, the scope of the invention being indicated by the appended claims, and all changes which come within the meaning and range of equivalency are intended to be embraced therein.

What is claimed is:

1. A method for screening to identify a compound with anti-human immunodeficiency virus type 1 (HIV-1) activity, the method comprising:
   (1) contacting HIV-1 infected cells and target cells with a candidate compound, wherein the target cells are susceptible to HIV-1 infection; and
   (2) measuring cell-to-cell transmission of HIV-1 in the presence and absence of the candidate compound,
   wherein cell-to-cell transmission of HIV-1 is measured by tracking mitochondrial movement from the HIV-1 infected cells to the target cells, and a reduction in mitochondrial movement from the HIV-1 infected cells to the target cells in the presence of the candidate compound relative to the absence of the candidate compound indicates that the candidate compound is an inhibitor of cell-to-cell HIV-1 transmission.

2. The method of claim 1, wherein the candidate compound is a mitochondrial inhibitor.

3. The method of claim 2, wherein the candidate compound is a mitochondrial inhibitor and a protease inhibitor.

4. The method of claim 1, wherein the candidate compound is a modulator of cytoskeletal processes.

5. The method of claim 4, wherein the cytoskeletal processes relate to actin or microtubule polymerization or depolymerization.

6. The method of claim 1, further comprising measuring HIV-1 cytopathogenic effects.

7. The method of claim 1, wherein mitochondria being tracked for movement from the HIV-1 infected cells to the target cells are cell-free mitochondria in culture.

8. The method of claim 1, wherein mitochondria being tracked for movement from the HIV-1 infected cells to the target cells are cell-free mitochondria purified from HIV-1 infected cells or culture media wherein the HIV-1 infected cells were grown.

9. The method of claim 6, wherein the HIV-1 cytopathogenic effects comprise virological synapse, syncytia formation, and infectious cell centers.

10. A method for screening to identify a compound that blocks human immunodeficiency virus type 1 (HIV-1) transmission, the method comprising:
   (1) providing mitochondria purified from HIV-1 infected cells;
   (2) contacting the mitochondria purified from HIV-1 infected cells and target cells with a candidate compound, wherein the target cells are susceptible to HIV-1 infection; and
   (3) measuring transmission of HIV-1 from the mitochondria to the target cells in the presence and absence of the candidate compound, wherein a reduction in transmission of HIV-1 in the presence of the candidate compound relative to the absence of the candidate compound indicates that the candidate compound is an inhibitor of mitochondria-mediated HIV-1 transmission.

* * * * *